United States Patent [19]
Marlin

[11] Patent Number: 5,934,903
[45] Date of Patent: Aug. 10, 1999

[54] NEEDLE AND METHOD FOR INJECTING HEATED THERMOPLASTIC MATERIAL INTO A DENTAL CAVITY

[76] Inventor: Jay Marlin, 69 Stoneledge Rd., So. Dartmouth, Mass. 02748

[21] Appl. No.: 08/976,917

[22] Filed: Nov. 24, 1997

[51] Int. Cl.⁶ .................................................. A61G 5/02
[52] U.S. Cl. .............................. 433/81; 604/239; 604/240
[58] Field of Search .................................. 433/81, 89, 90; 604/239, 240, 241, 242, 243

[56] References Cited

U.S. PATENT DOCUMENTS

| | | | |
|---|---|---|---|
| 860,555 | 7/1907 | Middaugh | 433/81 |
| 918,774 | 4/1909 | Schimmel | 604/241 |
| 1,189,735 | 7/1916 | Quintin | 433/81 |
| 1,402,011 | 1/1922 | Ostrov | 604/241 |
| 1,403,020 | 1/1922 | Everett | 604/241 |
| 1,667,454 | 4/1928 | Brix | 604/242 |
| 1,757,680 | 5/1930 | Neil | 604/242 |
| 2,512,568 | 6/1950 | Saffir | 604/239 |
| 2,752,919 | 7/1956 | Gabriel | 604/414 |
| 3,611,573 | 10/1971 | Crawford et al. | 433/81 |
| 3,802,433 | 4/1974 | Raven | 604/283 |
| 4,043,335 | 8/1977 | Ishikawa | 604/190 |
| 4,357,136 | 11/1982 | Herskovitz et al. | 433/224 |
| 4,852,768 | 8/1989 | Bartsch | 222/46 |
| 4,994,033 | 2/1991 | Shockey et al. | 604/101 |
| 5,002,535 | 3/1991 | Gross | 604/164 |
| 5,400,666 | 3/1995 | Song | 73/864 |
| 5,484,417 | 1/1996 | Waitz et al. | 604/165 |
| 5,637,101 | 6/1997 | Shillington | 604/242 |

*Primary Examiner*—John J. Wilson
*Attorney, Agent, or Firm*—Hamilton, Brook, Smith & Reynolds, P.C.

[57] ABSTRACT

A hollow jointless needle formed from a single piece of conductive metal for injecting thermoplastic material into a dental cavity includes a flange for securing the needle to an injection device. The flange extends transversely relative to the longitudinal axis of the needle. A first needle portion having a first diameter extends from the flange along the longitudinal axis. A second needle portion extending along the longitudinal axis is connected to the first needle portion by a first transition region. The second needle portion has a second diameter which is smaller than the first diameter of the first needle portion.

23 Claims, 4 Drawing Sheets

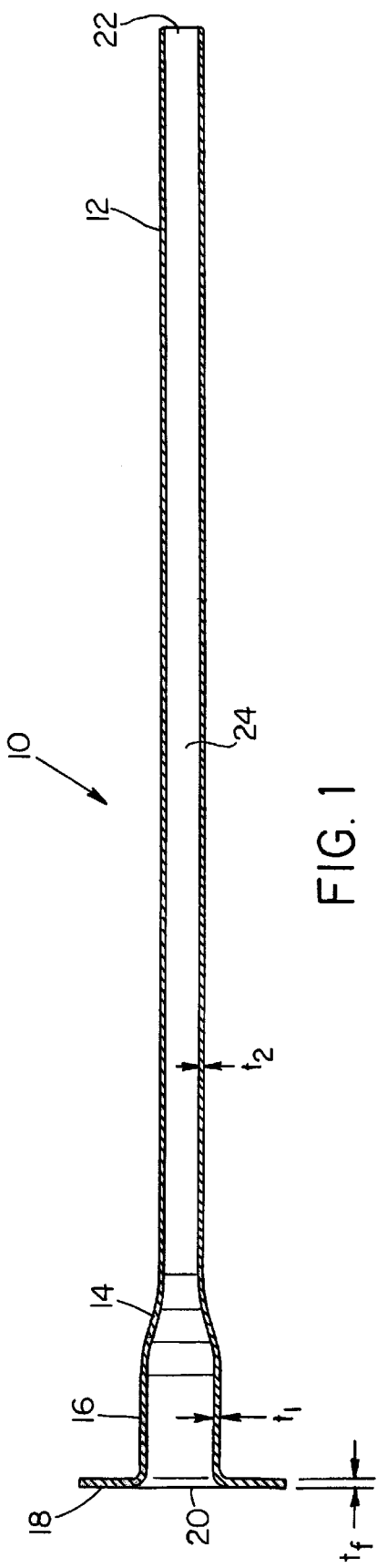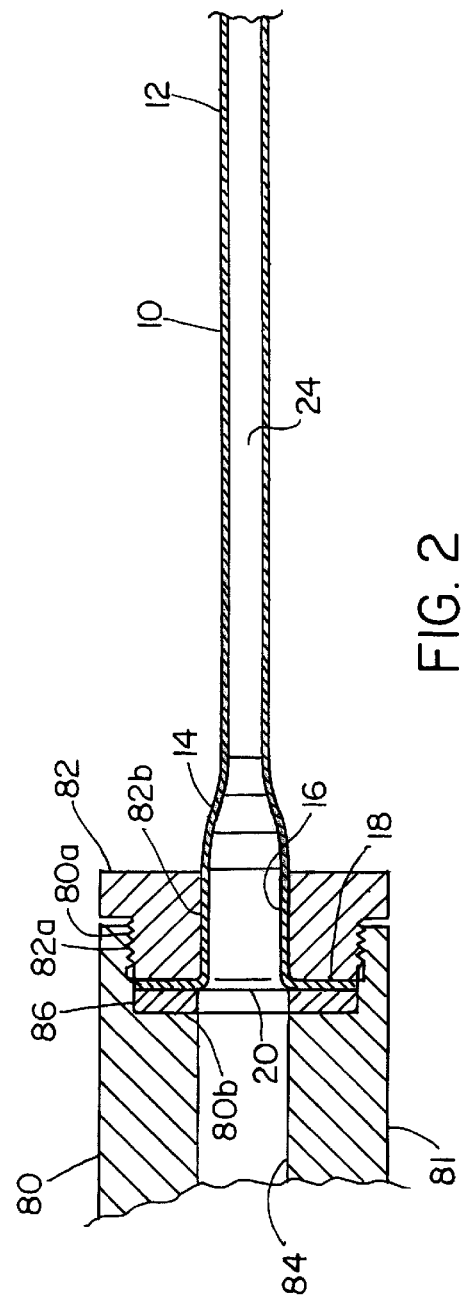

NEEDLE AND METHOD FOR INJECTING HEATED THERMOPLASTIC MATERIAL INTO A DENTAL CAVITY

BACKGROUND OF THE INVENTION

In the field of dentistry, one method for obturating root canal cavities involves injecting heated thermoplastic material, typically gutta-percha, into the dental cavity with a dental thermoplastic injection device. The injection device is typically a syringe-like instrument having a hollow needle through which the thermoplastic is ejected when the needle is inserted into the dental cavity. The needle is of high thermal conductivity material such as gold, silver, copper or aluminum to assume thermal conductance from a heater in the injection device to maintain the fluidity of the gutta-percha in the needle. See U.S. Pat. No. 4,357,136.

The needle is usually formed from two separate pieces which are joined together. The first piece is a narrow elongate needle portion made of the high thermal conductivity metal such as silver about 1 inch long with a constant diameter between 18 and 30 gauge. The second piece is a threaded hub portion which is brazed to the needle portion. The hub portion allows the needle to be attached to the injection device by screwing the hub portion into the body of the injection device. A drawback with this design is that the joint between the needle and the hub portions may break when the needle is bent within a convoluted dental cavity. Another drawback with the design is that the process for manufacturing the needle is relatively slow and expensive.

SUMMARY OF THE INVENTION

The present invention provides a one piece needle for a dental thermoplastic injection device that does not easily break when bent within a convoluted dental cavity and which is also suitable for manufacture with high speed automated operations.

The present invention is directed to a hollow jointless needle formed from a single piece of conductive metal for injecting thermoplastic material into a dental cavity. The needle extends along a longitudinal axis and includes a flange extending transversely relative to the longitudinal axis for securing the needle to an injection device. The needle has different diameters along its length. Specifically, a first needle portion having a first diameter extends from the flange along the longitudinal axis. A second needle portion extending along the longitudinal axis is a continuation of the first needle portion from a first transition region. In other words, the first transition region connects the second needle portion to the first needle portion. The second needle portion has a second diameter which is smaller than the first diameter of the first needle portion.

In preferred embodiments, the second needle portion is about 20 gauge. In addition, the needle is made from a metal having a coefficient of thermal conductivity greater than about 200 Btu/(hr)(ft$^2$)(°F./ft) such as gold, silver, copper and aluminum with silver being the most preferable. The first and second needle portions each have an outer wall with the wall of the second needle portion having a thickness that is less than the wall thickness of the first needle portion. The flange is planar with a thickness which is greater than the wall thickness of the first needle portion and extends perpendicularly to the longitudinal axis.

The larger diameter of the first needle portion reduces stress from the second needle portion to the flange by distributing stress over the larger diameter of the first needle portion. The thicker wall of the first needle portion further distributes stress from the second needle portion to the flange and also maintain a high thermal conductivity along its length.

In one preferred embodiment, the needle further includes a third needle portion extending along the longitudinal axis. The third needle portion is connected to the second needle portion by a second transition region. The third needle portion has a third diameter which is smaller than the second diameter of the second needle portion wherein the third needle portion is about 23 gauge and the second needle portion is about 20 gauge. The outer wall of the third needle portion has a thickness that is less than the wall thickness of the second needle portion.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 1 is a side sectional view of the present invention needle.

FIG. 2 is a side sectional view of the present invention needle secured to a dental thermoplastic injection device.

DETAILED DESCRIPTION OF THE INVENTION

Figure 4:
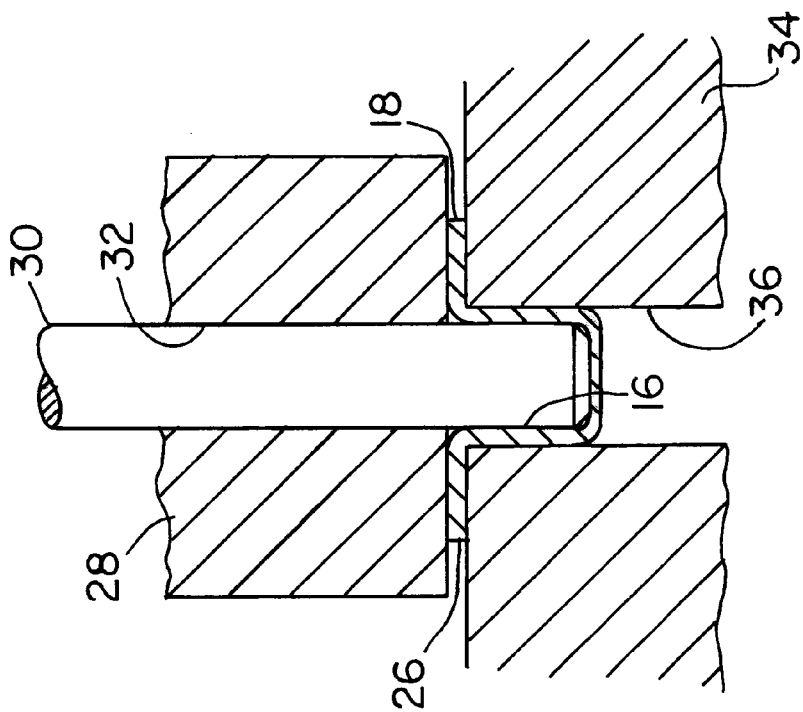
FIGS. 3–6 depict steps employed in a preferred method for forming the present invention needle.

Referring to FIG. 1, needle 10 is a one piece seamless needle that is employed with a syringe-like dental thermoplastic injection device 80 (FIG. 2) for injecting heated thermoplastic material into a dental cavity such as a root canal. Needle 10 is formed from a single piece of metal having high conductivity such as silver. A central passageway 24 extends through needle 10 along the longitudinal axis of needle 10. Needle 10 includes a circular flange 18 from which a short first hollow needle portion 16 extends at a right angle. A longer second hollow needle portion 12 is connected to the first needle portion 16 by a tapering hollow transition region 14. The second needle portion 12 has a diameter that is smaller than the first needle portion 16. The diameter of transition region 14 tapers down in size from the first needle portion 16 to the second needle portion 12. The inlet 20 to needle 10 extends through flange 18 into passageway 24 and the outlet 22 extends from passageway 24 through the end of the second needle portion 12. As the diameter of needle 10 decreases from the proximal end to the distal end, the wall thickness of needle 10 also decreases. The first needle portion 16 has a wall thickness $t_1$ which is greater than that of prior art needles while the second needle portion 12 has a wall thickness of standard dimensions for a particular needle gauge.

In use, referring to FIG. 2, needle 10 first must be secured to the distal end of dental thermoplastic injection device 80. Injection device 80 includes a passageway 84 through which heated thermoplastic is forced from injection device 80. Passageway 84 extends into a recess 80b at the distal end of injection device 80. Typically, the wall 81 surrounding passageway 84 contains electrical heating elements for heating and maintaining the thermoplastic (often gutta-percha) in a molten state. The flange 18 of needle 10 is inserted within recess 80b, and if needed, a washer 86 of high conductivity metal can be inserted between flange 18 and the bottom of recess 80b for improved sealing. A retaining nut 82 having a central opening 82b is fitted over first needle portion 16 against flange 18. Retaining nut 82 locks flange 18 within recess 80b by engaging threads 82a of nut 82 with mating threads 80a of recess 80b. The bottom surface of retaining nut 82 compresses flange 18 against the bottom of the recess 80b which seals flange 18 to passageway 84. As a result, needle 10 is physically and conductively coupled to injection device 80. Once flange 18 is locked in place, inlet 20 of needle 10 is positioned in line with passageway 84 of injection device 80 such that heated thermoplastic ejected from passageway 84 of injection device 80 can be forced through needle 10.

The diameter and wall thickness of second needle portion 12 is small enough to allow second needle portion 12 to be inserted into and bent (typically up to 45°) within convoluted dental cavities without crimping. If required, needle 10 can be bent 360° without crimping or breaking. Stresses on second needle portion 12 caused by bending are distributed over the larger diameter of first needle portion 16 before reaching flange 18, thereby reducing stresses and breakage at the flange 18. Further strength is provided by the increased wall thickness of first needle portion 16. When the thermoplastic is injected through needle 10 into a dental cavity, the thick wall of first needle portion 16 enables needle 10 to conduct more heat from injection device 80 to the thermoplastic flowing through needle 10 than possible with prior art needles, thereby keeping the thermoplastic at a higher temperature. In addition, the large diameter of first needle portion 16 allows a larger mass of thermoplastic to occupy passageway 24 than in prior art needles so that the thermoplastic within needle 10 can retain heat better, resulting in a slower cooling process. These features maintain the thermoplastic in a more fluid state than previously possible with prior art needles, thus improving the flow of the thermoplastic material through needle 10 and requiring less force to eject the thermoplastic material.

A more detailed description of needle 10 now follows. Needle 10 is preferably made from a single piece of silver (at least 90%) but alternatively can be made of other high conductivity metals such as gold, copper or aluminum which have coefficients of thermal conductivity greater than about 200 Btu/(hr)(ft$^2$)(°F./ft). Needle 10 is a 20 gauge needle 1.13 inches long. More specifically, the needle size is 20 gauge at second needle portion 12 and outlet 22. Flange 18 preferably is 0.156+0.000/−0.002 inches in diameter with a thickness $t_f$ of 0.010+/−0.001 inches. Flange 18 extends radially beyond first needle portion 16 transversely relative to the longitudinal axis of needle 10 about 0.086/0.096 inches. This provides sufficient surface area for retaining nut 82 to engage flange 18 for securing needle 10 to injection device 80. The first needle portion 16 is preferably about 0.1 inches long with an 0.060/0.068 inch outer diameter and a 0.043+/−0.0005 inch inner diameter resulting in a wall thickness $t_1$ of about 0.0083 to 0.0128 inches. The transition region 14 is about 0.05 inches long and gradually reduces in diameter from the first needle portion 16 to the second needle portion 12. The second needle portion 12 is just about 1 inch long with a 0.035+/−0.001 inch outer diameter and a 0.023+/−0.001 inch inner diameter resulting in a wall thickness $t_2$ of about 0.005 to 0.007 inches. As a result, the wall thickness of the first needle portion 16 is less than the thickness of flange 18 and the wall thickness of second needle portion 12 is less than the first needle portion 16. Although particular dimensions have been given for needle 10, alternatively, other suitable dimensions can be employed. For example, needle 10 can be between about 20 to 40 mm long (0.70 to 1.57 inches). In needles longer than 30 mm, the first needle portion 16 and transition region 14 can be longer than previously described.

Figure 3:
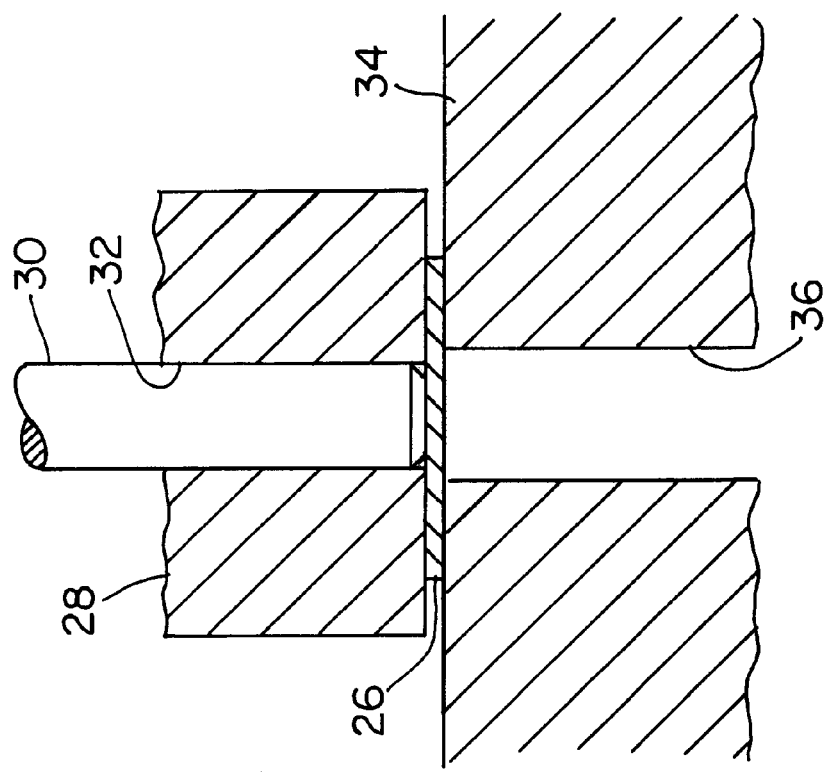

Needle 10 is preferably made by the method depicted in FIGS. 3–6. Referring to FIG. 3, a circular blank 26 of silver is positioned over a bottom die 34. Bottom die 34 includes a circular opening 36. A top die 28 is brought down on top of blank 26. Top die 28 includes a mandrel 30 which slides within a bore 32. Mandrel 30 is positioned above blank 26.

Referring to FIG. 4, the mandrel 30 is moved downwardly. The movement of mandrel 30 plastically deforms and draws material from the center of blank 26 downward into the opening 36 within bottom die 34. This forms flange 18 and the first needle portion 16 of needle 10. More than one drawing operation can be conducted to form first needle portion 16, if needed.

Figure 5:
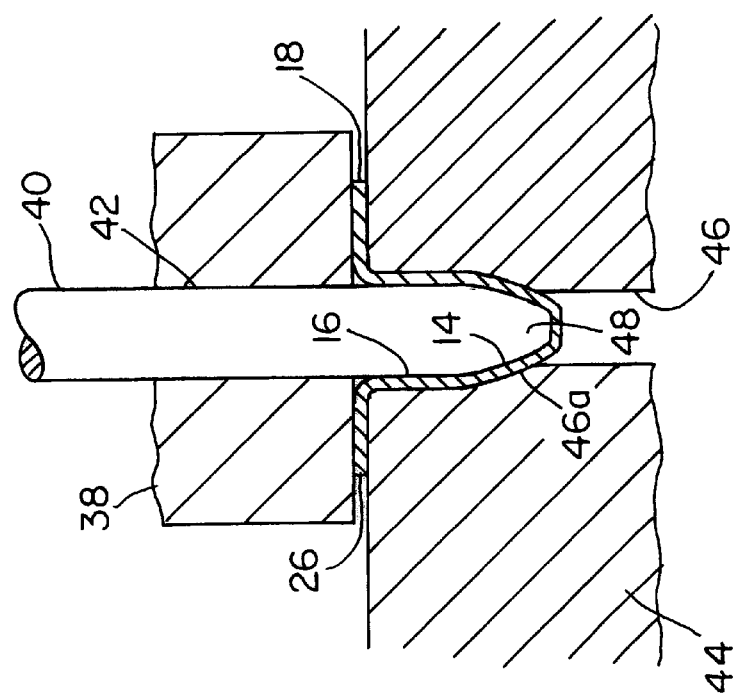

Referring to FIG. 5, the flange 18 of blank 26 is positioned on the upper surface of bottom die 56 and first needle portion 16 is positioned within the opening 46 of bottom die 44. Opening 46 has a section corresponding to first needle portion 16 of needle 10 and a tapered section 46a having the same contours as transition region 14. Top die 38 is brought down on top of flange 18. Top die 38 includes a mandrel 40 which slides within a bore 42. Mandrel 40 has a tapered tip 48 matching the inner contour of transition region 14. Mandrel 40 is moved downwardly through bore 42 into opening 46 to plastically deform the material at the bottom of first needle portion 16 against the tapered section 46a of opening 46 to form transition region 14. More than one drawing operation can be conducted to form transition region 14.

Figure 6:
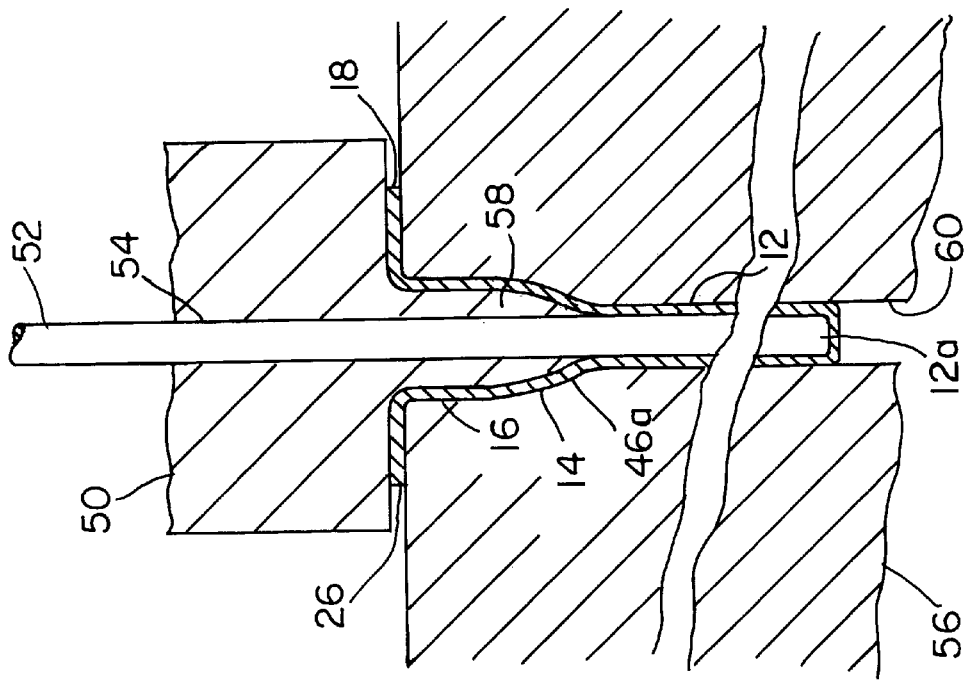

Referring to FIG. 6, flange 18 of blank 26 is positioned on the upper surface of bottom die 56 and first needle portion 16 is positioned within the opening 60 of bottom die 56. Opening 60 has a section corresponding to first needle portion 16, a tapered section 46a corresponding to transition region 14 and a smaller diameter section corresponding to second needle portion 12. Top die 50 is brought down on top of flange 18. Top die 50 includes a lower portion 58 which is shaped to fit within the first needle portion 16 and transition region 14. Top die 50 also includes a mandrel 52 which slides within a bore 54 extending through top die 50. Mandrel 52 is moved downwardly through bore 54 to plastically deform and draw material at the bottom of transition region 14 further downward through the small diameter portion of opening 60 to form second needle portion 12. The sequential drawing operations result in a jointless seamless one piece needle 10 with diameters and wall thicknesses that decrease toward the tip of needle 10. More than one drawing operation can be used to form the final length of second needle portion 12. Once second needle portion 12 is finished, the closed distal end 12a is cut off. If needed, flange 18 can be trimmed. In the sequence discussed above, transition region 14 is formed before second needle portion 12. Alternatively, transition region 14 can be formed after second needle portion 12 has been formed.

Figure 7:
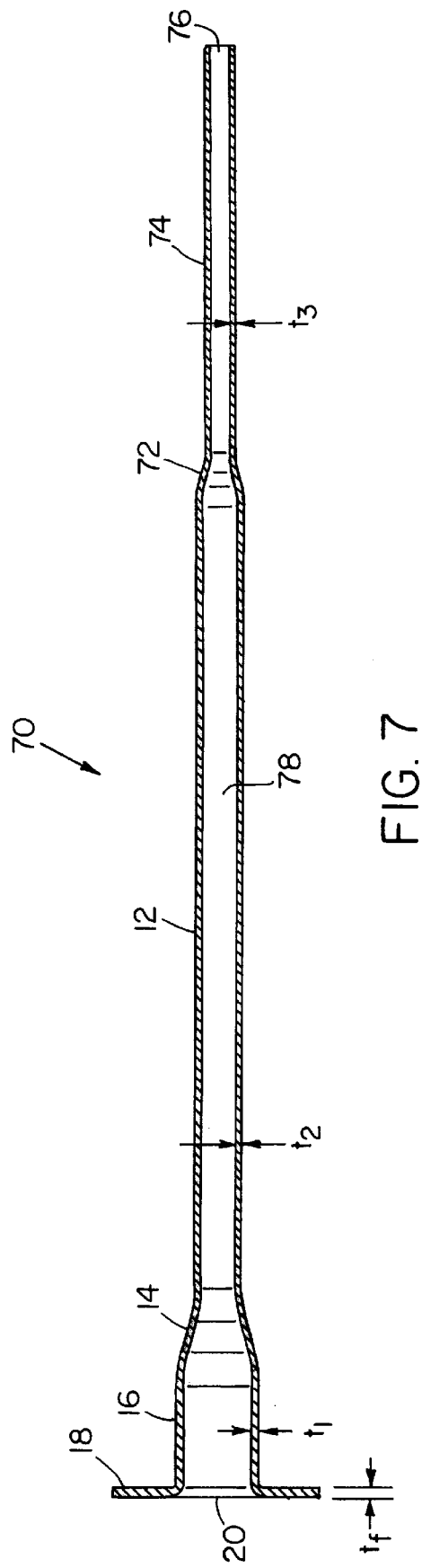
FIG. 7 is a side sectional view of another preferred needle.

Referring to FIG. 7, needle 70 is another preferred needle. Needle 70 differs from needle 10 in that needle 70 is a 23 gauge needle 1.13 inches long. More specifically, needle 70 includes a third hollow needle portion 74 of 23 gauge which is connected to second needle portion 12 (20 gauge) by a second hollow tapering transition region 72. The third needle portion 74 is preferably about 0.35 inches long with an outer diameter of 0.025+/−0.001 inches and an inner diameter of 0.018+/−0.001 inches. This results in a wall thickness $t_3$ of about 0.0025 to 0.0045 inches. As a result, needle 70 has three needle portions which reduce in diameter and wall thickness along its longitudinal axis. Needle 70 has a passageway 78 extending therethrough along the longitudinal axis of needle 70. Passageway 78 has an inlet 20 extending through flange 18 and an outlet 76 extending through the distal end of third needle portion 74. Needle 70 is formed in a manner similar to that needle 10 except that additional drawing steps are required for forming the second transition region 72 and third needle portion 76. Needle 70 is slightly more flexible than needle 10 and is useful for insertion into smaller and more convoluted dental cavities. Although the third needle portion 74 has been described to be about 0.35 inches long, third needle portion 74 can be shorter or longer depending upon the application.

Although drawings and particular dimensions have been provided for 20 and 23 gauge needles, needles made in accordance with the present invention can range from about 20 to 30 gauge. As a result, the diameters and wall thicknesses of first needle portion 16, second needle portion 12 and third needle portion 74 (when needed) are sized in accordance with the particular needle gauge desired.

EQUIVALENTS

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

For example, although the thermoplastic is typically gutta-percha, alternatively, other suitable dental compatible thermoplastics can be employed. In addition, although flange 18 is shown and described to be flat, alternatively, flange 18 can be other suitable shapes such as conical. Furthermore, the present invention needle can be made without a step in the elongate needle portion.

What is claimed is:

1. A hollow jointless needle extending along a longitudinal axis formed from a single piece of conductive metal for injecting thermoplastic material into a dental cavity comprising:
    a flange for securing the needle to an injection device extending transversely relative to the longitudinal axis;
    a first needle portion having a first diameter extending from the flange along the longitudinal axis; and
    a second needle portion extending along the longitudinal axis connected to the first needle portion by a first transition region, the second needle portion having a second diameter which is smaller than the first diameter of the first needle portion the first and second needle portions each having a wall, the wall of the second needle portion having a thickness that is less than the wall thickness of the first needle portion and the flange having a thickness which is greater than the thickness of the wall of the first needle portion.

2. The needle of claim 1 in which the flange is planar and extends perpendicularly to the longitudinal axis.

3. The needle of claim 1 in which the second needle portion is about 20 gauge.

4. The needle of claim 1 in which the needle is made from a metal having a coefficient of thermal conductivity greater than about 200 Btu/(hr)(ft$^2$)(°F./ft).

5. The needle of claim 1 in which the needle is made from a metal is selected from the group consisting of gold, silver, copper and aluminum.

6. The needle of claim 1 in which the needle is made of silver.

7. The needle of claim 1 further comprising a third needle portion extending along the longitudinal axis, the third needle portion being connected to the second needle portion by a second transition region, the third needle portion having a third diameter which is smaller than the second diameter of the second needle portion.

8. The needle of claim 7 in which the first, second and third needle portions each have a wall, the wall of the second needle portion having a thickness that is less than the wall thickness of the first needle portion and the wall of the third needle portion having a thickness that is less than the wall thickness of the second needle portion.

9. The needle of claim 7 in which the second needle portion is about 20 gauge and the third needle portion is about 23 gauge.

10. A hollow jointless needle extending along a longitudinal axis formed from a single piece of conductive metal for injecting thermoplastic material into a dental cavity comprising:
    a planar flange for securing the needle to an injection device extending perpendicularly relative to the longitudinal axis;
    a first needle portion having a first diameter extending from the flange along the longitudinal axis, the first needle portion having a wall, the flange having a thickness which is greater than the wall thickness of the first needle portion; and
    a second needle portion extending along the longitudinal axis connected to the first needle portion by a first transition region, the second needle portion having a second diameter which is smaller than the first diameter of the first needle portion, the second needle portion having a wall with a thickness that is less than the wall thickness of the first needle portion.

11. The needle of claim 10 in which the second needle portion is about 20 gauge.

12. The needle of claim 10 in which the needle is made from a metal having a coefficient of thermal conductivity greater than about 200 Btu/(hr)(ft$^2$)(°F./ft).

13. The needle of claim 10 further comprising a third needle portion extending along the longitudinal axis, the third needle portion being connected to the second needle portion by a second transition region, the third needle portion having a third diameter which is smaller than the second diameter of the second needle portion.

14. The needle of claim 13 in which the third needle portion has a wall, the wall of the second needle portion having a thickness that is less than the wall thickness of the first needle portion and the wall of the third needle portion having a thickness that is less than the wall thickness of the second needle portion.

15. The needle of claim 13 in which the second needle portion is about 20 gauge and the third needle portion is about 23 gauge.

16. A method of reducing bending stress in a needle for a dental thermoplastic injection device comprising the steps of:
    forming the needle from a single piece of conductive metal, the needle being hollow and jointless and extending along a longitudinal axis, the needle including a flange extending transversely relative to the longitudinal axis for securing the needle to the injection device;

providing the needle with a first needle portion having a first diameter extending from the flange along the longitudinal axis;

providing the needle with a second needle portion extending along the longitudinal axis and connected to the first needle portion by a first transition region, the second needle portion having a second diameter, the first diameter of the first needle portion being larger than the second diameter of the second needle portion for reducing stress from the second needle portion to the flange by distributing stress over the larger diameter of the first needle portion; and providing the first needle portion with a wall that is thicker than that of the second needle portion for further distributing stress from the second needle portion to the flange.

17. A method of filling a dental cavity with a needle coupled to a dental thermoplastic injection device comprising the steps of:

forming the needle from a single piece of conductive metal, the needle being hollow and jointless and extending along a longitudinal axis, the needle including a flange extending transversely relative to the longitudinal axis for securing the needle to the injection device;

providing the needle with a first needle portion having a first diameter extending from the flange along the longitudinal axis;

providing the needle with a second needle portion extending along the longitudinal axis and connected to the first needle portion by a first transition region, the second needle portion having a second diameter, the first diameter of the first needle portion being larger than the second diameter of the second needle portion for reducing stress from the second needle portion to the flange by distributing stress over the larger diameter of the first needle portion;

providing the first needle portion with a wall that is thicker than that of the second needle portion for further distributing stress from the second needle portion to the flange;

inserting the needle into the dental cavity; and injecting thermoplastic through the needle into the dental cavity.

18. A hollow jointless needle extending along a longitudinal axis formed from a single piece of conductive metal for injecting thermoplastic material into a dental cavity comprising:

a flange for securing the needle to an injection device extending transversely relative to the longitudinal axis;

a first needle portion having a first diameter extending from the flange along the longitudinal axis; and a second needle portion extending along the longitudinal axis connected to the first needle portion by a first transition region, the second needle portion having a second diameter which is smaller than the first diameter of the first needle portion, the first and second needle portions each having a wall, the wall of the second needle portion having a thickness that is less than the wall thickness of the first needle portion and the flange having a thickness which is greater than the thickness of the wall of the first needle portion, the needle being made from a metal having a coefficient of thermal conductivity greater than about 200 Btu/(hr)(ft$^2$)(°F./ft).

19. A hollow jointless needle extending along a longitudinal axis formed from a single piece of conductive metal for injecting thermoplastic material into a dental cavity comprising:

a flange for securing the needle to an injection device extending transversely relative to the longitudinal axis;

a first needle portion having a first diameter extending from the flange along the longitudinal axis; and a second needle portion extending along the longitudinal axis connected to the first needle portion by a first transition region, the second needle portion having a second diameter which is smaller than the first diameter of the first needle portion, the first and second needle portions each having a wall, the wall of the second needle portion having a thickness that is less than the wall thickness of the first needle portion and the flange having a thickness which is greater than the thickness of the wall of the first needle portion, the needle being made from a metal selected from the group consisting of gold, silver, copper and aluminum.

20. A hollow jointless needle extending along a longitudinal axis formed from a single piece of conductive metal for injecting thermoplastic material into a dental cavity comprising:

a flange for securing the needle to an injection device extending transversely relative to the longitudinal axis;

a first needle portion having a first diameter extending from the flange along the longitudinal axis; and a second needle portion extending along the longitudinal axis connected to the first needle portion by a first transition region, the second needle portion having a second diameter which is smaller than the first diameter of the first needle portion, the first and second needle portions each having a wall, the wall of the second needle portion having a thickness that is less than the wall thickness of the first needle portion and the flange having a thickness which is greater than the thickness of the wall of the first needle portion, the needle being made of silver.

21. A hollow jointless needle extending along a longitudinal axis formed from a single piece of conductive metal for injecting thermoplastic material into a dental cavity comprising:

a flange for securing the needle to an injection device extending transversely relative to the longitudinal axis;

a first needle portion having a first diameter extending from the flange along the longitudinal axis;

a second needle portion extending along the longitudinal axis connected to the first needle portion by a first transition region, the second needle portion having a second diameter which is smaller than the first diameter of the first needle portion; and a third needle portion extending along the longitudinal axis, the third needle portion being connected to the second needle portion by a second transition region, the third needle portion having a third diameter which is smaller than the second diameter of the second needle portion.

22. The needle of claim 21 in which the first, second and third needle portions each have a wall, the wall of the second needle portion having a thickness that is less than the wall thickness of the first needle portion and the wall of the third needle portion having a thickness that is less than the wall thickness of the second needle portion.

23. The needle of claim 21 in which the second needle portion is about 20 gauge and the third needle portion is about 23 gauge.

* * * * *